(12) United States Patent
Ueno et al.

(10) Patent No.: US 6,995,010 B1
(45) Date of Patent: Feb. 7, 2006

(54) GENE TRANSFER METHOD

(75) Inventors: Takashi Ueno, Shiga (JP); Hajime Matsumura, Shiga (JP); Keiji Tanaka, Shiga (JP); Tomoko Iwasaki, Shiga (JP); Mitsuhiro Ueno, Shiga (JP); Kei Fujinaga, Hokkaido (JP); Kiyozo Asada, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 249 days.

(21) Appl. No.: 10/111,708

(22) PCT Filed: Oct. 23, 2000

(86) PCT No.: PCT/JP00/07373

§ 371 (c)(1),
(2), (4) Date: Apr. 29, 2002

(87) PCT Pub. No.: WO01/32899

PCT Pub. Date: May 10, 2001

(30) Foreign Application Priority Data

Oct. 29, 1999 (JP) .................................. 11-308839

(51) Int. Cl.
| | | |
|---|---|---|
| C12N 5/16 | (2006.01) | |
| C12N 15/861 | (2006.01) | |
| C12N 15/864 | (2006.01) | |
| A61K 48/00 | (2006.01) | |

(52) U.S. Cl. .................... 435/320.1; 435/325; 435/455; 435/456; 435/457; 435/462; 435/466; 424/93.2

(58) Field of Classification Search ............... 424/93.2; 435/91.4, 320.1, 455, 456, 462, 466, 457, 435/325
See application file for complete search history.

(56) References Cited

FOREIGN PATENT DOCUMENTS

WO    WO 9810086    3/1998

OTHER PUBLICATIONS

Orkin et al., Report and recommendations of the Panel to Assess the NIH Investment in Research on Gene Therapy, issued by the U.S. National Institutes of Health on Dec. 7, 1995.*
Verma et al., "Gene therapy—promises, problems and prospects," Nature 389: 239-242, Sep. 18, 1997.*
Rosenberg et al., "Gene therapist, heal thyself," Science 287: 1751, Mar. 10, 2000.*
Chejanovsky et al., "Mutagenesis of an AUG codon in the adeno-associated virus rep gene: effects of viral DNA replication," Virol. 173 : 120-128, 1989.*
Recchia., et al. "Site-specific Integration mediation by a hybrid adenovirus/adeno-associated virus vector," Proc. Natl. Acad. Sci. USA 96:2615-2620 (1999).
Ogasawara, et al. "Highly regulated expression of adeno-associated virus large Rep proteins in stable 293 cell lines using the Cre/loxP switching system," Journal of General Virology, 80:2477-2480 (1999).
Ueno, et al., "Site-Specific Integration of a Transgene Mediated by a Hybrid Adenovirus/Adeno-Associated Virus Vector Using the Cre/loxP-Expression-Switching System," Biochemical and Biophysical Research Communications 273:473-478 (2000).

* cited by examiner

Primary Examiner—Scott D. Priebe
(74) Attorney, Agent, or Firm—Browdy and Neimark, PLLC

(57) ABSTRACT

A method of transferring a foreign gene into cells, characterized by involving: the step of transferring into the cells with the use of an adenovirus vector, a first nucleic acid, which has a sequence provided with adeno-associated virus-origin ITRs in both sides of the target foreign gene to be transferred, and a second nucleic acid, which has an adeno-associated virus-origin rep gene and a promoter for expressing this gene and carries a stuffer sequence inserted thereinto sandwiched in two recombinase recognition sequences and located between the rep gene and the promoter; and the step of expressing the Rep protein under the action of recombinase in the cells obtained in the above step to thereby integrate the target foreign gene into the chromosomal DNA.

7 Claims, 1 Drawing Sheet

Fig. 1

No viral infection

AxCANCre

AxCALNLRep78

AxITRZ

AxCANCre+AxCALNLRep78

AxCANCre+AxITRZ

AxCALNLRep78+AxITRZ

AxCANCre+AxCALNLRep78+AxITRZ

GENE TRANSFER METHOD

TECHNICAL FIELD

The present invention relates to a method that increases the efficiency of gene transfer into target cells and enables efficient transformation of the target cells, as well as a series of techniques related therewith, in the fields of medicine, cell technology, genetic engineering, developmental technology and the like.

BACKGROUND ART

Mechanisms of a number of human diseases have been elucidated. The recombinant DNA techniques and the techniques for transferring a gene into cells have rapidly progressed. Under these circumstances, protocols for somatic gene therapies for treating severe genetic diseases have been recently developed. More recently, attempts have been made to apply the gene therapy not only to treatment of the genetic diseases but also to treatment of viral infections such as AIDS as well as cancers.

Viral vectors currently used in general include retroviral vectors, adenoviral vectors and adeno-associated viral (AAV) vectors. A retroviral vector can be readily prepared and integrate a foreign gene into the chromosomal DNA of a target cell. Therefore, it is useful for gene therapy for which a long-term gene expression is desired. However, since a foreign gene is integrated at random sites in a chromosomal DNA, cancer or the like may be potentially caused if a retroviral vector is used. Furthermore, since a retroviral vector cannot infect cells in resting phase, the types of target cells are limited.

Although there were problems about the method for preparing adenoviral vectors, a convenient preparation method has been developed. The vector can efficiently infect many types of cells including cells in resting phase. However, since it does not have a mechanism for integrating a foreign gene into the chromosomal DNA of a target cell, the expression of the foreign gene is usually transient.

An AAV vector can infect cells in resting phase and has a nature to integrate a foreign gene specifically at the AAVS1 site on human chromosome 19. Thus, it is expected that a gene transferred using the AAV vector is expressed for a long period in a cell without potential risk. However, there are practical problems associated with the AAV vectors that the preparation of AAV is complicated and the size of a gene that can be transferred into cells is very small.

As described above, conventional viral vectors used for gene therapy have their own advantages and disadvantages. No gene transfer method that enables convenient handling, high gene transfer efficiency and long-term expression of a transferred gene was known. A system that satisfies these properties has been desired.

An attempt was made to develop such a system. In the system, a region of AAV required for the site-specific integration of a foreign gene is incorporated into an adenoviral vector which has advantages of high gene transfer efficiency and easy preparation of a high-titer vector in order to overcome the drawback of the adenoviral vectors that they cannot integrate a foreign gene into the chromosomal DNA of a target cell (see, for example, U.S. Pat. No. 5,843,742).

However, since a Rep protein, which is encoded by the region of AAV required for the site-specific integration of a foreign gene, inhibits the proliferation of an adenovirus, an adenovirus having the region cannot proliferate. Therefore, it is impossible to prepare such a vector and, in consequence, gene transfer using such a vector is practically infeasible.

Recchia et al. tried to solve the above-mentioned problem by using a hepatic cell-specific promoter, α1AT promoter, for expressing a rep gene (Recchia et al., Proceedings of the National Academy of Sciences of the USA, 96:2615–2620 (1999)). Since the α1AT promoter is a hepatic cell-specific promoter, it does not operate in a virus-producer cell to be used for the preparation of an adenoviral vector (a producer cell). Therefore, the rep gene contained in the adenoviral vector is not expressed and the proliferation of the adenoviral vector is not inhibited.

However, the method of Recchia et al. has a drawback that the cell type in which a foreign gene can be integrated into the chromosomal DNA is limited to the hepatic cell because the promoter used for expressing the rep gene is a hepatic cell-specific one.

The prior art has drawbacks as described above. A method which results in high gene transfer efficiency, by which a high-titer vector is readily prepared, which enables the integration of a foreign gene into the chromosomal DNA of a target cell, and which can be used to transfer a foreign gene into a wide variety of cell types has been desired.

OBJECTS OF INVENTION

The main object of the present invention is to provide a gene transfer method which results in high gene transfer efficiency, by which a high-titer vector is readily prepared, which enables the integration of a foreign gene into the chromosomal DNA of a target cell, and which can be used to transfer a foreign gene into a wide variety of cell types.

SUMMARY OF INVENTION

As a result of intensive studies, the present inventors have found that a foreign gene can be transferred into a wide variety of cell types and integrated into the chromosomal DNAs by using an expression control system that utilizes a recombinase and a recombinase recognition sequence such as the Cre/loxP expression control system. Specifically, the present inventors have established a method and constructed a system used for the method. In the method, the expression of a rep gene contained in an adenoviral vector in a virus-producer cell is repressed by inserting a stuffer sequence put between recombinase recognition sequences. On the other hand, in the target cell having the adenoviral vector being transferred, the stuffer sequence put between the recombinase recognition sequences is removed through the action of a recombinase, the rep gene is expressed, and a foreign gene flanked by ITRs transferred into the target cell can be integrated into the chromosomal DNA of the target cell. Thus, the present invention has been completed.

The present invention provides a method in which (1) a first nucleic acid which has a sequence in which ITRs from AAV are positioned on both sides of a foreign gene of interest, and (2) a second nucleic acid in which a stuffer sequence put between two recombinase recognition sequences is positioned between a rep gene from AAV and a promoter are transferred into a cell using an adenoviral vector, and the foreign gene of interest is efficiently integrated into the chromosomal DNA of a wide variety of target cell types in a site-specific manner through the action of a recombinase in the cell.

Specifically, when the above-mentioned two nucleic acids are transferred into a target cell expressing a recombinase, the stuffer sequence put between two recombinase recognition sequences in the second nucleic acid is removed through the action of the recombinase in the target cell, and the rep gene is expressed. The foreign gene in the first nucleic acid is integrated into the chromosomal DNA of the target cell through the action of a Rep protein expressed from the rep gene and the ITRs in the first nucleic acid.

The present invention is outlined as follows. The first aspect of the present invention relates to a method for transferring a foreign gene into a cell, the method comprising:
(a) transferring into a cell using an adenoviral vector:
  (1) a first nucleic acid which has a sequence in which ITRs from adeno-associated virus are positioned on both sides of a foreign gene of interest to be transferred; and
  (2) a second nucleic acid which has a rep gene from adeno-associated virus and a promoter for expressing the rep gene and in which a stuffer sequence put between two recombinase recognition sequences is inserted between the rep gene and the promoter; and
(b) expressing a Rep protein in the cell obtained in step (a) through the action of a recombinase to integrate the foreign gene of interest into the chromosomal DNA of the cell.

The second aspect of the present invention relates to a system for transferring a foreign gene into a cell, which contains:
(1) an adenoviral vector containing a first nucleic acid which has a sequence in which ITRs from adeno-associated virus are positioned on both sides of a gene of interest to be transferred; and
(2) an adenoviral vector containing a second nucleic acid which has a rep gene from adeno-associated virus and a promoter for expressing the rep gene and in which a stuffer sequence put between two recombinase recognition sequences is inserted between the rep gene and the promoter.

The third aspect of the present invention relates to a system for transferring a foreign gene into a cell, which contains an adenoviral vector containing:
  a first nucleic acid which has a sequence in which ITRs from adeno-associated virus are positioned on both sides of a gene of interest to be transferred; and
  a second nucleic acid which has a rep gene from adeno-associated virus and a promoter for expressing the rep gene and in which a stuffer sequence put between two recombinase recognition sequences is inserted between the rep gene and the promoter.

The fourth aspect of the present invention relates to a transformed cell into which a foreign gene is transferred by the method of the first aspect.

The fifth aspect of the present invention relates to a transformed cell into which a foreign gene is transferred using the system of the second or third aspect.

BRIEF DESCRIPTION OF DRAWINGS

FIG. 1: a figure illustrating the results of dot blot hybridization for detecting site-specific integration.

DETAILED DESCRIPTION OF THE INVENTION

The present invention will be explained in detail.

Adenoviruses are linear double-stranded DNA viruses. The size of the genomic DNA is about 36 kb. A terminal protein encoded by the virus is covalently bound to the 5'-termini on both ends of the genomic DNA to form a DNA-terminal protein complex (DNA-TPC).

There is no specific limitation concerning the adenovirus used as a vector according to the present invention. For example, human adenovirus type 2 or 5 each exhibiting high proliferation efficiency and little pathogenicity can be used. A nonproliferative adenovirus constructed by deleting the E1 region involved in the replication of the virus from the adenoviral genome is used as a vector. Since an adenovirus lacking the E1 region lacks its competence to proliferate, proliferation of the virus which may cause a disease state in a target cell does not occur. Therefore, such an adenovirus is preferable according to the present invention in view of safety.

There is no specific limitation concerning the deletion of a viral genome as long as the resulting one can function as a vector. An adenovirus from which the E3 region, which is not indispensable to the proliferation of the virus in cultured cells, is partially or entirely removed in addition to the above-mentioned E1 region can also be used.

An adenovirus lacking the E1 region or both the E1 region and the E3 region can proliferate in the 293 cell derived from human embryonal kidney, which permanently expresses the genes in the E1 region.

In view of reduction in production of immunogens which may cause side effects, an adenovirus from which the E2 region and/or the E4 region is further deleted in addition to the E1 and E3 regions can also be used. Also, a gutless adenovirus vector (Parks et al., Proceedings of the National Academy of Sciences of the USA, 93:13565–13570 (1996)) from which the viral genes are fully removed can be used.

Such an adenovirus can proliferate in a cell that expresses the genes contained in the deleted region or upon coinfection with a helper virus that contains the deleted region.

A first nucleic acid used according to the present invention is a nucleic acid having a sequence in which inverted terminal repeats (ITRs) from adeno-associated virus (AAV) are positioned on both sides of a foreign gene of interest to be transferred. Although it is not intended to limit the present invention, the first nucleic acid is preferably used being incorporated in an adenoviral vector. The gene of interest contained in this nucleic acid is integrated into the genome of a target cell in a site-specific manner through the action of the ITRs from AAV and a Rep protein expressed from a second nucleic acid described below.

ITRs are T-shaped hairpin structures each consisting of 145 bases located on both ends of the single-stranded DNA of AAV. They contain sequences indispensable to integration of the viral genome at the AAVS1 site on chromosome 19 of human as its host (Yukihiko Hirai, Jikken Igaku (Experimental Medicine), 12 (15):1811–1816 (1994)). ITRs used according to the present invention are not specifically limited as long as they have activities of integrating at the AAVS1 site, and may be subjected to substitution, deletion, insertion or addition.

There is no specific limitation concerning a foreign gene to be inserted between two ITRs. It may be any gene of which the transfer is desired. Genes encoding enzymes or other proteins connected with diseases to be treated, and genes encoding functional nucleic acid molecules such as antisense nucleic acids, ribozymes or decoys are exemplified. There is also no specific limitation concerning the origin of the gene. The gene may be one derived from an organism species that is the same as or different from that of the cell into which the gene is to be transferred, chemically synthesized one, or a combination of thereof. Appropriate regulatory elements such as a promoter and an enhancer for regulating the expression of the gene may be added to the gene.

Although it is not intended to limit the present invention, the desired size of the foreign gene of interest to be inserted between two ITRs is, for example, in case of one lacking the E1 and E3 regions, about 7.2 kb or less in view of packaging of a recombinant adenoviral vector. In case of a gutless adenovirus vector, the size is desirably 37 kb or less.

The promoter to be used for the first nucleic acid according to the present invention is not specifically limited as long as it can express a gene of interest in a target cell. For example, such promoters include CAG promoter, SRα promoter, EF1α promoter, CMV promoter and PGK promoter, and can selected depending on the purpose. If a tissue-specific promoter is used, a gene of interest can be expressed in a tissue-specific manner. For example, expression can be conducted in a hepatic cell-specific manner by using liver-specific α1AT promoter, in a skeletal muscle-specific manner by using skeletal muscle-specific α-actin promoter, in a nerve-specific manner by using nerve-specific enolase promoter, in a vascular endothelial cell-specific manner by using vascular endothelial cell-specific tie promoter, in a gastric cancer-specific manner by using gastric cancer-specific CEA promoter, or in a hepatic cancer-specific manner by using hepatic cancer-specific AFP promoter.

A second nucleic acid according to the present invention is one in which a promoter/a recombinase recognition sequence/a stuffer sequence/a recombinase recognition sequence/a rep gene from AAV are arranged in this order. Although it is not intended to limit the present invention, the second nucleic acid is preferably used being incorporated in an adenoviral vector. This nucleic acid expresses a rep gene in a target cell. The rep gene is required for the integration of a foreign gene of interest contained in the above-mentioned first nucleic acid into the chromosomal DNA of the target cell.

The rep gene, which has cytotoxicity and an activity of inhibiting proliferation of an adenovirus, is not expressed in a cell for the proliferation of an adenovirus (a producer cell) which does not contain a recombinase. This is because a stuffer sequence exists between the promoter and the rep gene in this nucleic acid. Thus, it can be used to proliferate the virus in large quantities. On the other hand, the stuffer sequence put between the recombinase recognition sequences is excised through the action of a recombinase in any target cell expressing the recombinase. As a result, the promoter is placed adjacent to the initiation codon of the rep gene, enabling the expression of the rep gene.

The Rep region of AAV encodes four proteins, Rep78, Rep68, Rep52 and Rep40. Among these, Rep78 protein or Rep68 protein (called large Rep) is indispensable to the integration of the AAV genome at the AAVS1 site on human chromosome 19. The rep gene used according to the present invention is not specifically limited as long as it has an activity of integrating a foreign gene of interest contained in the nucleic acid of the first aspect into the chromosomal DNA of a target cell. For example, it may be one encoding Rep78 protein, Rep68 protein, or a protein subjected to substitution, deletion, addition or insertion in Rep78 protein or Rep68 protein without losing the activity.

The region encoding Rep78 protein and Rep68 protein also encodes Rep52 protein and Rep40 protein. Rep52 protein and Rep40 protein have activities of inhibiting the proliferation of an adenovirus. Thus, it is desirable to modify the rep gene used according to the present invention by site-directed mutagenesis or the like so as to prevent the expression of Rep52 protein and Rep40 protein. For example, the expression of Rep52 protein and Rep40 protein can be prevented by changing the 225th amino acid residue in Rep78 protein from methionine to glycine.

There is no specific limitation concerning a promoter to be used for the second nucleic acid according to the present invention as long as it can exhibit its activity in a target cell and express a rep gene after removal of a stuffer sequence. The promoter can be selected depending on the purpose. The promoter used for the second nucleic acid can be selected regardless of its expression in a producer cell because the expression of the promoter is almost completely repressed in the producer cell due to the existence of the stuffer sequence.

For example, p5 promoter from AAV, SRα promoter, EF1α promoter, CMV promoter, SV40 promoter, a promoter from a virus such as 5' LTR promoter from murine leukemia virus, and a fused promoter having a portion from a virus such as CAG promoter are known to operate in a number of cell types regardless of tissues. Therefore, they are preferable if many cell types are to be targeted.

Furthermore, a gene of interest can be transferred in a tissue-specific manner by selecting a tissue-specific promoter. There is no specific limitation concerning the tissue or the cell into which a gene of interest is to be transferred as long as an adenovirus can infect it and the AAVS1 site is present on its chromosome. A gene of interest can be transferred into substantially all human tissues or cells by selecting a promoter at will. For example, skeletal muscle-specific α-actin promoter, nerve-specific enolase promoter or vascular endothelial cell-specific tie promoter can be selected if the gene of interest is to be transferred into skeletal muscle, nerve or vascular endothelial cells, respectively. In addition, if a suicide gene is to be transferred targeting a cancer cell, gastric cancer-specific CEA promoter, hepatic cancer-specific AFP promoter or the like may be selected.

In the system of the present invention, as the expression of a rep gene is increased, the efficiency of integration of a foreign gene of interest into a chromosomal DNA may be increased. However, on the other hand, it is considered that the toxicity against a target cell may also be increased. Since the toxicity of the product of the rep gene, the Rep protein, to a cell varies depending on the type of the cell, it is necessary to optimize the expression level of the rep gene depending on the target cell. For this purpose, a promoter having an optimal expression strength for the target cell may be selected. For example, it is known that the expression strengths of the above-mentioned CAG, CMV and SV40 promoters in many cell types are as follows: CAG promoter>CMV promoter>SV40 promoter. Thus, for example, SV40 promoter, CAG promoter or CMV promoter can be used if a cell type that exhibits high, low or moderate sensitivity to the cytotoxicity of the Rep protein is used as a target cell, respectively.

Furthermore, the expression of p5 promoter from AAV is repressed in the presence of the Rep protein. If a promoter like p5 promoter is used, once the rep gene is expressed, the activity of the promoter is then repressed by the Rep protein expressed from the rep gene. As a result, overexpression of the rep gene is repressed. Thus, the toxicity due to the Rep protein can be limited to a minimum.

A stuffer sequence used according to the present invention is a sequence that intervenes between a promoter and a rep gene in a second nucleic acid to repress the expression of the rep gene from the promoter. There is no specific limitation concerning the stuffer sequence as long as it intervenes between the promoter and the rep gene to repress the expression of the rep gene. However, it desirably contains a terminator sequence, a poly(A) sequence or the like in view of strict expression control. Since the expression from the promoter used for the second nucleic acid is almost completely repressed by the stuffer sequence, it is expected that a recombinant adenovirus is efficiently produced in a producer cell. The repression of the promoter due to the stuffer sequence in the producer cell can be confirmed at the level of transcription (e.g., using Northern blotting or RT-PCR), or by determining the ability of the producer cell to produce recombinant viruses.

Expression control systems that utilize recombinases and recombinase recognition sequences include the following: Cre/loxP expression control system (Kanegae et al., Nucleic Acids Research, 23:3816–3821 (1995)); an expression control system that utilizes a recombinase encoded by FLP gene from yeast $2\mu$ plasmid (Broarch et al., Cell, 29:227–234 (1982)); and an expression control system that utilizes a recombinase encoded by R gene from *Zygosaccharomyces rouxii* pSR1 plasmid (Matsuzaki et al., Molecular and Cellular Biology, 8:955–962 (1988)). Although it is not intended to limit the present invention, the expression control system used according to the present invention is preferably the Cre/loxP expression control system in view of recombination efficiency.

There is no specific limitation concerning the recombinase recognition sequence to be used according to the present invention as long as a recombinase can recognize it to remove a stuffer sequence put between the sequences. The recombinase recognition sequence is exemplified by the loxP sequence which is a sequence recognized by the recombinase Cre in the Cre/loxP expression control system.

The loxP sequence is a sequence recognized by Cre, a site-specific recombinase encoded by *Escherichia coli* P1 phage (Abremski et al., Journal of Biological Chemistry, 259:1509–1514 (1984), Hoess et al., Proceedings of the National Academy of Sciences of the USA, 81:1026–1029 (1984), Hoess et al., Journal of Molecular Biology, 181:351–362 (1985)). The recombinase Cre specifically recognizes a minimal unit in the loxP sequence consisting of 34 bases to effect cleavage of DNA and strand displacement between two loxP sequences. Specifically, if two loxp sequences exist on the same molecule in the same direction, a DNA sequence put between the loxP sequences is excised as a circular molecule through the action of the recombinase Cre (an excision reaction). Only the minimal unit as described in Hoess et al (Proceedings of the National Academy of Sciences of the USA, 81:1026–1029 (1984)) may be used as a loxP sequence according to the present invention.

There is no specific limitation concerning the loxP sequence used according to the present invention as long as the recombinase Cre recognizes it to effect an excision reaction. It may be the wild-type loxP sequence from *Escherichia coli* P1 phage or a mutant sequence subjected to substitution, deletion, addition or insertion to the extent that the recombinase Cre recognizes it to effect an excision reaction. Such a mutant sequence is exemplified by loxP2272, loxP5171, loxP2271, loxP3171, loxP5272 or loxP5372 as described in Lee et al., Gene, 216:55–65 (1998).

There is no specific limitation concerning the recombinase used according to the present invention. A recombinase that can recognize a recombinase recognition sequence in a second nucleic acid to effect an excision reaction may be selected and used. For example, a site-specific recombinase from *Escherichia coli* P1 phage, Cre, can be used to excise a stuffer sequence put between loxP sequences. The recombinase used according to the present invention is not specifically limited as long as it recognizes a recombinase recognition sequence to exhibit a DNA recombination activity. For example, it may be one having an amino acid sequence of a wild-type recombinase subjected to substitution, deletion, addition or insertion to the extent that it exhibits the activity. Alternatively, one to which a nuclear transport signal is added for facilitating nuclear transport in a cell may be used.

There is no specific limitation concerning the method for expressing a recombinase in a target cell. For example, a nucleic acid encoding a recombinase can be transferred into a cell for expression. Although the method for transferring such a nucleic acid is not specifically limited, a transfer method using an adenoviral vector is preferable because the adenoviral vector results in high gene transfer efficiency and a high-titer vector can be readily prepared for it.

There is no specific limitation concerning the promoter used for a vector for expressing a recombinase as long as it can express a recombinase gene to induce the expression of Rep and enable the integration of a foreign gene of interest. For example, it may be a promoter having an activity in various tissues such as CAG promoter, SRα promoter, EF1α promoter, CMV promoter or PGK promoter. Alternatively, it may be a tissue-specific promoter which operates only in a specific tissue such as the above-mentioned liver-specific α1AT promoter. If a tissue-specific promoter is used, it is possible to specifically integrate a foreign gene only into the chromosomal DNAs of cells in a specific tissue.

An adenoviral vector containing a first nucleic acid and an adenoviral vector containing a second nucleic acid may be transferred into a cell expressing a recombinase in order to transfer a gene of interest into a target cell. The two vectors may be transferred simultaneously or separately. Alternatively, a single adenoviral vector containing both the first and second nucleic acids may be transferred into a cell. Specifically, an adenoviral vector containing the elements of the first nucleic acid (a gene of interest put between ITRs from AAV) and the elements of the second nucleic acid (a promoter/a recombinase recognition sequence/a stuffer sequence/a recombinase recognition sequence/a rep gene from AAV) on a single vector may be transferred.

If a recombinase is to be expressed from a recombinase gene transferred into a cell, an adenoviral vector containing a first nucleic acid, an adenoviral vector containing a second nucleic acid, and a vector for transferring the recombinase gene into a cell may be transferred into the target cell. The three vectors may be transferred simultaneously or separately. The first and second nucleic acids may be contained in a single adenoviral vector. In this case, this vector is used in combination with a vector for transferring a recombinase gene into a cell. Alternatively, the first nucleic acid and the recombinase gene may be contained in a single adenoviral vector. In other words, an adenoviral vector constructed to contain the elements of the first nucleic acid (a gene of interest put between ITRs from AAV) and a recombinase gene in a single vector, and an adenoviral vector containing the second nucleic acid may be used.

A recombinase (e.g., the recombinase Cre) expressed in a target cell recognizes two recombinase recognition sequences (e.g., the loxP sequences) in a second nucleic acid, and removes a stuffer sequence put between the two recombinase recognition sequences through an excision reaction. As a result, a promoter in the second nucleic acid is placed adjacent to a rep gene, resulting in the expression of the rep gene by the action of the promoter. A gene of interest put between ITRs in a first nucleic acid is integrated at the AAVS1 site on chromosome 19 of the target cell by the action of a Rep protein produced from the second nucleic acid. The gene of interest integrated into the chromosome of the target cell as described above is stably retained in the target cell and stably expressed for a long period. Furthermore, since any promoter can be used as a promoter for expressing a rep gene, a gene of interest can be expressed in any cell.

One can be readily prepared a high-titer virus for the adenoviral vector used according to the present invention like for conventional adenoviruses. The method for preparing an adenoviral vector according to the present invention is exemplified by the COS-TPC method (Proceedings of the National Academy of Sciences of the USA, 93:1320 (1996)). Using this method, a vector according to the present invention can be efficiently prepared without complicated procedures.

An adenoviral vector used according to the present invention can efficiently infect a number of cell types including those in resting phase like an adenovirus. Therefore, it can be utilized for gene therapies for various tissues or cells. Furthermore, since it can integrate a foreign gene in a site-specific manner like AAV, it can be used to express the foreign gene for a long period without the risk of developing cancer or the like due to integration at random sites.

Furthermore, unlike retroviral vectors, a foreign gene of interest can be expressed using any promoter for the adenoviral vector to be used according to the present invention. Since a rep gene can also be expressed using any promoter, there is no specific limitation concerning the cell type to which the present invention can be applied, and the foreign gene can be transferred into any type of target cell. In addition, unlike AAV, a large-sized foreign gene of interest can be inserted.

Thus, the gene transfer method of the present invention is an excellent system which overcomes all the drawbacks associated with conventional systems including limited target cell type, inefficient infection, short expression period and difficult expression control. Thus, it can be used for all gene therapies whose effects were limited due to the limitation of conventional methods and remarkable therapeutic effects are expected.

There is no specific limitation concerning the disease to be subjected to gene therapy using the gene transfer method of the present invention. The method can be utilized to treat a genetic disease for which a congenital genetic abnormality is observed, a viral infection such as AIDS, and cancer. Since a gene transferred using the gene transfer method of the present invention is integrated into the chromosomal DNA of a target cell, it is possible to express a foreign gene for a long period. Thus, the method is particularly useful for treatment of a genetic disease for which a congenital genetic abnormality is observed such as adenosine deaminase deficiency, muscular dystrophy or phenylketonuria.

Furthermore, the gene transfer method of the present invention is useful not only for gene therapy but also for obtaining cells having various foreign genes in vitro. The thus obtained cells having genes being transferred are useful for production of useful substances, development of disease models and the like.

Furthermore, one can conveniently carry out the present invention by using a kit containing an adenoviral vector having a first nucleic acid and an adenoviral vector containing a second nucleic acid according to the present invention. For example, the kit contains a component for constructing an adenoviral vector having a first nucleic acid into which a selected foreign gene of interest is incorporated, and an adenoviral vector containing a second nucleic acid. A vector for expressing a recombinase may be further included in the kit. Additionally, a cultured cell for preparing an adenovirus (a producer cell), a medium, a cell culture plate and the like may be included.

The gene transfer method of the present invention can be carried out, for example, as follows.

An adenoviral vector containing a first nucleic acid can be prepared as follows.

The rep region and the cap region are removed from a plasmid containing a genomic DNA from AAV, and a foreign gene to be transferred is inserted into the resulting product. The source of the foreign gene to be transferred is not specifically limited. It may be prepared from a genome or a recombinant, amplified by a PCR, or chemically synthesized. The plasmid prepared as described above has an integration unit that consists of a sequence in which ITR sequences from AAV are positioned on both sides of the foreign gene.

Next, the integration unit is prepared from the resulting plasmid by digestion with a restriction enzyme. The integration unit is inserted into a cosmid pAxcw (a cosmid containing almost entire adenoviral genome lacking the E1 and E3 genes) contained in Adenovirus Expression Vector Kit (Takara Shuzo, hereinafter referred to as Kit 1) at its SwaI site. A recombinant adenovirus that contains the integration unit (a first nucleic acid) can be prepared from the resulting recombinant cosmid using Kit 1.

An adenoviral vector containing a second nucleic acid can be prepared as follows.

A region encoding Rep78 protein is prepared from the plasmid containing the genomic DNA from AAV. The region encoding Rep78 protein can be obtained by PCR amplification using the above-mentioned plasmid as a template or treatment of the plasmid with a restriction enzyme.

A region encoding Rep52 protein which represses the proliferation of an adenovirus is contained in the DNA fragment obtained as described above. Then, the nucleotide sequence for the 225th amino acid residue in Rep78 protein is changed from ATG which corresponds to methionine to GGA which corresponds to glycine using site-directed mutagenesis in order to eliminate the expression from that region.

Next, the mutant rep 78 gene fragment is inserted into a cosmid pAxCALNLw that contains an adenoviral genome, a promoter/a loxP sequence/a stuffer sequence/a loxP sequence/a SwaI cloning site at the SwaI site to prepare a cosmid containing a promoter/a loxP sequence/a stuffer sequence/a loxP sequence/a mutant rep78 gene fragment (a second nucleic acid). An adenovirus that contains a promoter/a loxP sequence/a stuffer sequence/a loxp sequence/a mutant rep78 gene fragment (a second nucleic acid) can be prepared from the resulting cosmid using Kit 1.

A cosmid pAxCALNLw attached to Adenovirus Cre/loxP-Regulated Expression Vector Kit (Takara Shuzo, hereinafter referred to as Kit 2) can be used for the preparation of an adenovirus containing a second nucleic acid. It is prepared by inserting, in this order, a loxP sequence, a neomycin resistance gene, an SV40 virus poly(A) signal, a loxP sequence and a SwaI linker into pAxCAwt attached to Kit 1 at its SwaI site. pAxCAwt is a cosmid prepared by inserting CAG promoter sequence into the above-mentioned cosmid pAxcw. In this case, the neomycin resistance gene and the SV40 virus poly(A) signal correspond to a stuffer sequence.

An adenoviral vector for expressing cre gene can be prepared using Kit 1 from a recombinant cosmid which is obtained by inserting the cre gene into the cosmid pAxcw at the SwaI site as described for the first and second vectors. Alternatively, an adenoviral vector for expressing the cre gene, AxCANCre, as described in Kanegae et al., Nucleic Acids Research, 23:3816–3821 (1995) may be used. The adenoviral vector AxCANCre attached to Adenovirus Cre/loxP-Regulated Expression Vector Kit (Takara Shuzo, Kit 2) may be used. A method for determining the titer of a recombinant adenovirus obtained as described above is known in the art. For example, the titer can be determined according to the method of Kit 1.

The three types of adenoviral vectors obtained as described above are transferred into a target cell according to a conventional method. In the cell, a recombinase Cre generated as a result of the expression of the cre gene removes the stuffer sequence put between the loxP sequences. Subsequently, Rep protein generated as a result of the expression of the rep gene integrates the foreign gene of interest positioned between the ITRs into the chromosomal DNA of the cell. It is possible to confirm if the foreign gene of interest is integrated at the AAVS1 site in the chromosomal DNA of the target cell in a site-specific manner by carrying out a PCR. In the PCR, a chromosomal DNA prepared from the target cell for gene transfer is used as a template, and a primer that anneals to the integration unit and a primer that anneals to the AAVS1 site are used.

The frequency of specific integration in unit cell number (integration efficiency) can be determined, for example, according to the following method.

A first nucleic acid in which a drug resistance gene (e.g., a neomycin resistance gene) is inserted in the integration unit is prepared. If this first nucleic acid is integrated into the chromosomal DNA of a target cell, daughter cells generated as a result of proliferation of the target cell exhibit drug resistance because they always have the drug resistance gene. On the other hand, if the integration into the chromosomal DNA of the target cell does not occur, the daughter cells generated as a result of proliferation of the target cell become drug sensitive because the drug resistance gene transferred into the cell is not retained in the daughter cells. Thus, when the target cell is cultured in a medium containing a drug (e.g., neomycin) for a long period after transferring the first nucleic acid having the drug resistance gene being inserted into the target cell, only cells in which integration has been occurred proliferate and form colonies (drug resistant colonies).

The efficiency of integration of a foreign gene into a target cell can be determined as a ratio of the number of drug resistant colonies (Drug resistant) to the number of colonies formed after culturing for a long period in a medium without a drug (Total) according to the following equation:

(Integration efficiency)=(Drug resistant)÷(Total).

It should be noted that the integration efficiency determined as described above includes that of non-site-specific integration. The efficiency of site-specific integration can be determined as follows: several drug resistant colonies are picked up; specific integration is confirmed by the above-mentioned method using a PCR; a ratio of colonies with site-specific integration in drug resistant colonies is determined; the efficiency of site-specific integration of a foreign gene into a target cell is then determined by multiplying the above-mentioned integration efficiency by the determined ratio.

EXAMPLES

The following Examples further illustrate the present invention in detail but are not to be construed to limit the scope thereof.

Example 1

Preparation of Recombinant Adenoviral Vector 1.1 Preparation of first vector (adenoviral vector containing first nucleic acid)

An adenoviral vector AxAAVZ that contains β-galactosidase gene as a foreign gene was prepared as follows.

A plasmid pAV1 (ATCC 37215) contains a genomic DNA from AAV having a nucleotide sequence of SEQ ID NO:1. A double-stranded EcoRV linker consisting of a synthetic DNA having a nucleotide sequence of SEQ ID NO:4 and a synthetic DNA having a nucleotide sequence of SEQ ID NO:5 was inserted into pAV1 at the AvaII site (nucleotide number 191 in SEQ ID NO:1). A double-stranded EcoRV linker consisting of two synthetic DNA strands each having a nucleotide sequence of SEQ ID NO:6 being annealed each other was further inserted into pAV1 at the NcoI site (nucleotide number 4485 in SEQ ID NO:1). As a result, a plasmid pAV1E5 was obtained. A DNA fragment (βgal expression unit) which comprises CMV promoter, β-galactosidase gene and SV poly(A) signal was obtained by digesting a plasmid pβgal (Clontech) with EcoRI and HindIII. After blunting the ends of this fragment using DNA Blunting Kit (Takara Shuzo), the resulting fragment was inserted into pAV1E5 at its EcoRV site. The thus obtained plasmid was digested with BglII to prepare the βgal expression unit put between ITRs from AAV (hereinafter referred to as an integration unit). The integration unit was inserted into a cosmid pAxcw contained in Adenovirus Expression Vector Kit (Takara Shuzo, Kit 1) at its SwaI site. A recombinant adenovirus AxITRZ was prepared from the resulting recombinant cosmid using Kit 1.

1.2 Preparation of second vector (adenoviral vector containing second nucleic acid)

An adenoviral vector AxCALNLRep78 for expressing a rep gene in a target cell was prepared as follows.

A PCR was carried out using the plasmid pAV1 as a template as well as a primer REPF having a nucleotide sequence of SEQ ID NO:2 and a primer REPR having a nucleotide sequence of SEQ ID NO:3 to amplify a region of nucleotide numbers from 313 to 2205 in SEQ ID NO:1 which contained rep78 gene. The PCR was carried out using TaKaRa Taq (Takara Shuzo).

The resulting amplified DNA fragment contained rep52 gene which represses proliferation of an adenovirus in addition to the rep78 gene. The 225th amino acid residue in Rep78 was changed from methionine to glycine in order to eliminate the expression of this gene. Specifically, ATG at nucleotide numbers 993–995 in SEQ ID NO:1 was changed to GGA using the plasmid pAV1 as a template, an oligonucleotide having a nucleotide sequence of SEQ ID NO:11 and Mutan Super Expression Km (Takara Shuzo). An amplified DNA fragment was then obtained as described above.

The mutant amplified DNA fragment was inserted into a cosmid pAxCALNLw attached to Adenovirus Cre/loxP-Regulated Expression Vector Kit (Takara Shuzo, Kit 2) at its SwaI site. Then, an adenovirus AxCALNLRep78 was prepared using Kit 1.

1.3 Third vector (vector for expressing cre gene)

An adenoviral vector AxCANCre attached to Adenovirus Cre/loxP-Regulated Expression Vector Kit (Takara Shuzo, Kit 2) was used for expressing cre gene.

Example 2

Infection Experiments

HeLa cells (ATCC CCL-2) were cultured in a 24-well cell culture plate (Iwaki Glass). DMEM medium containing 10% fetal calf serum (both from Bio Whittaker) was used for culturing the cells. Infections were carried out according to the instructions attached to Kit 1 using one of the recombinant adenoviruses AxCANCre, AxCALNLRep78 and AxITRZ alone or a combination thereof. After culturing for two days, insertion of the integration unit at the AAVS1 site in an infected cell was examined as follows.

A genomic DNA was prepared from an infected cell according to the method as described in the instructions attached to Kit 1. A PCR was carried out using the resulting genomic DNA as a template as well as a primer 81 (SEQ ID NO:7) which anneals to the integration unit and a primer 1722 (SEQ ID NO:8) which anneals to the AAVS1 site. One µl each of the PCR products was spotted onto a nylon membrane (Hybond-N, Amersham). Dot blot hybridization was carried out using DIG Labeling & Detection Kit (Boehringer-Mannheim) to detect site-specific integration. A probe was prepared using a human genomic DNA as a template, primers 79 and 80 having nucleotide sequences of SEQ ID NOS:9 and 10, respectively, and PCR DIG Probe Synthesis Kit (Boehringer-Mannheim). The resulting probe has the nucleotide sequence of the AAVS1 site. The results are shown in FIG. 1. As shown in FIG. 1, site-specific integration of the foreign gene did not occur when infections were carried out using one or two of the three recombinant viruses AxCANCre, AxCALNLRep78 and AxITRZ. Site-specific integration was observed only in the cell co-infected with the three recombinant viruses.

Example 3

Next, infection experiments were carried out using a human lung-derived cell line A549 (ATCC CCL-185) or a human liver-derived cell line HepG2 (ATCC HB-8065) as a target cell to examine transfer of a foreign gene into a cell other than the HeLa cell.

Infections were carried out as described in Example 2 using one of the recombinant adenoviruses AxCANCre, AxCALNLRep78 and AxITRZ obtained in Example 1 alone or a combination thereof. Site-specific integration was detected according to the method as described in Example 2.

As a result, for both the A549 cell and the HepG2 cell, site-specific integration of the foreign gene did not occur when infections were carried out using one or two of the three recombinant viruses AxCANCre, AxCALNLRep78 and AxITRZ, and was observed only in the cell co-infected with the three recombinant viruses as observed for the HeLa cell.

These results suggest that a foreign gene can be integrated into not only the HeLa cell but also various human cells in a site-specific manner according to the method of the present invention.

INDUSTRIAL APPLICABILITY

The present invention provides a method for transferring a foreign gene in which the foreign gene is efficiently transferred into a human cell or a human individual and integrated specifically at the AAVS1 site on chromosome 19. The present invention is particularly useful for gene therapy.

Sequence Listing Free Text

SEQ ID NO:2: PCR primer designated as REPF to amplify Rep78 gene.

SEQ ID NO:3: PCR primer designated as REPR to amplify Rep78 gene.

SEQ ID NO:4: EcoRV linker.

SEQ ID NO:5: EcoRV linker.

SEQ ID NO:6: EcoRV linker.

SEQ ID NO:7: PCR primer designated as 82 which anneals with integration unit.

SEQ ID NO:8: PCR primer designated as 1722 which anneals with AAVS1 region.

SEQ ID NO:9: PCR primer designated as 80 to amplify AAVS1 region used as a probe.

SEQ ID NO:10: PCR primer designated as 80 to amplify AAVS1 region used as a probe.

SEQ ID NO:11: Designed oligonucleotide to introduce mutation into Rep78 gene.

We claim:

1. A system for transferring a foreign gene into a cell, which contains:
   a. a combination of:
      1. an adenoviral vector containing a first nucleic acid which has a sequence in which ITRs from adeno-associated virus are positioned on both sides of a gene of interest to be transferred; and
      2. an adenoviral vector containing a second nucleic acid which has a rep gene from adeno-associated virus in which the expression of Rep52 protein and Rep40 protein are prevented by changing the $225^{th}$ amino acid residue in Rep78 from methionine to glycine and a promoter for expressing the rep gene and in which a stuffer sequence put between two recombinase recognition sequences is inserted between the rep gene and the promoter; or
   b. an adenoviral vector containing:
      a first nucleic acid which has a sequence in which ITRs from adeno-associated virus are positioned on both sides of a gene of interest to be transferred; and
      a second nucleic acid which has a rep gene from adeno-associated virus and a promoter for expressing the rep gene and in which a stuffer sequence put between two recombinase recognition sequences is inserted between the rep gene and the promoter.

2. The system according to claim 1, which contains a vector for transferring a recombinase gene into a cell.

3. The system according to claim 2, wherein the vector for transferring a recombinase gene into a cell is an adenoviral vector.

4. The system according to claim 3, wherein the adenoviral vector containing the first nucleic acid, the adenoviral vector containing the second nucleic acid and the vector for transferring a recombinase gene into a cell are different each other.

5. The system according to claim 1, wherein the recombinase recognition sequences in the second nucleic acid are loxP nucleotide sequences, and the recombinase is Cre, a recombinase from *Escherichia coli* P1 phage.

6. A transformed cell into which a foreign gene is transferred using the system defined by claim 1.

7. A system for transferring a foreign gene into a cell, which system contains a combination of:
   a. an adenoviral vector containing a first nucleic acid which has a sequence in which ITRs from adeno-associated virus are positioned on both sides of a gene of interest to be transferred and a recombinase gene; and
   b. an adenoviral vector containing a second nucleic acid which has a rep gene from adeno-associated virus and a promoter for expressing the rep gene and in which a stuffer sequence put between two recombinase recognition sites is inserted between the rep gene and the promoter.

* * * * *

SEQUENCE LISTING

<160> NUMBER OF SEQ ID NOS: 11

<210> SEQ ID NO 1
<211> LENGTH: 4675
<212> TYPE: DNA
<213> ORGANISM: Adeno-associated Virus

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccatttt tgaagcggga     300
```

-continued

| | |
|---|---|
| ggtttgaacg cgcagccgcc atgccggggt tttacgagat tgtgattaag gtccccagcg | 360 |
| accttgacgg gcatctgccc ggcatttctg acagctttgt gaactgggtg gccgagaagg | 420 |
| aatgggagtt gccgccagat tctgacatgg atctgaatct gattgagcag gcacccctga | 480 |
| ccgtggccga gaagctgcag cgcgactttc tgacggaatg gcgccgtgtg agtaaggccc | 540 |
| cggaggccct tttctttgtg caatttgaga agggagagag ctacttccac atgcacgtgc | 600 |
| tcgtggaaac caccggggtg aaatccatgg ttttgggacg tttcctgagt cagattcgcg | 660 |
| aaaaactgat tcagagaatt taccgcggga tcgagccgac tttgccaaac tggttcgcgg | 720 |
| tcacaaagac cagaaatggc gccggaggcg ggaacaaggt ggtggatgag tgctacatcc | 780 |
| ccaattactt gctccccaaa acccagcctg agctccagtg ggcgtggact aatatggaac | 840 |
| agtatttaag cgcctgtttg aatctcacgg agcgtaaacg gttggtggcg cagcatctga | 900 |
| cgcacgtgtc gcagacgcag gagcagaaca agagaatca gaatcccaat tctgatgcgc | 960 |
| cggtgatcag atcaaaaact tcagccaggt acatggagct ggtcggtgg ctcgtggaca | 1020 |
| agggattac ctcggagaag cagtggatcc aggaggacca ggcctcatac atctccttca | 1080 |
| atgcggcctc caactcgcgg tcccaaatca aggctgcctt ggacaatgcg ggaaagatta | 1140 |
| tgagcctgac taaaaccgcc cccgactacc tggtgggcca gcagcccgtg gaggacattt | 1200 |
| ccagcaatcg gatttataaa attttggaac taaacgggta cgatcccaa tatgcggctt | 1260 |
| ccgtctttct gggatgggcc acgaaaaagt tcggcaagag gaacaccatc tggctgtttg | 1320 |
| ggcctgcaac taccgggaag accaacatcg cggaggccat agcccacact gtgcccttct | 1380 |
| acgggtgcgt aaactggacc aatgagaact ttcccttcaa cgactgtgtc gacaagatgg | 1440 |
| tgatctggtg ggaggagggg aagatgaccg ccaaggtcgt ggagtcggcc aaagccattc | 1500 |
| tcggaggaag caaggtgcgc gtggaccaga atgcaagtc ctcggcccag atagacccga | 1560 |
| ctcccgtgat cgtcacctcc aacaccaaca tgtgcgccgt gattgacggg aactcaacga | 1620 |
| ccttcgaaca ccagcagccg ttgcaagacc ggatgttcaa atttgaactc acccgccgtc | 1680 |
| tggatcatga ctttgggaag gtcaccaagc aggaagtcaa agactttttc cggtgggcaa | 1740 |
| aggatcacgt ggttgaggtg gagcatgaat tctacgtcaa aaagggtgga gccaagaaaa | 1800 |
| gacccgcccc cagtgacgca gatataagtg agcccaaacg ggtgcgcgag tcagttgcgc | 1860 |
| agccatcgac gtcagacgcg gaagcttcga tcaactacgc agacaggtac caaaacaaat | 1920 |
| gttctcgtca cgtgggcatg aatctgatgc tgtttccctg cagacaatgc gagagaatga | 1980 |
| atcagaattc aaatatctgc ttcactcacg gacagaaaga ctgtttagag tgctttcccg | 2040 |
| tgtcagaatc tcaacccgtt tctgtcgtca aaaaggcgta tcagaaactg tgctacattc | 2100 |
| atcatatcat gggaaaggtg ccagacgctt gcactgcctg cgatctggtc aatgtggatt | 2160 |
| tggatgactg catctttgaa caataaatga tttaaatcag gtatggctgc cgatggttat | 2220 |
| cttccagatt ggctcgagga cactctctct gaaggaataa gacagtggtg gaagctcaaa | 2280 |
| cctggcccac caccaccaaa gcccgcagag cggcataagg acgacagcag gggtcttgtg | 2340 |
| cttcctgggt acaagtacct cggacccttc aacggactcg caagggaga gccggtcaac | 2400 |
| gaggcagacg ccgcggccct cgagcacgta caaagcctac gaccggcagc tcgacagcgg | 2460 |
| agacaacccg tacctcaagt acaaccacgc cgacgcggga tttcaggagc gccttaaaga | 2520 |
| agatacgtct tttgggggca acctcggacg agcagtcttc caggcgaaaa agagggttct | 2580 |
| tgaacctctg ggcctggttg aggaacctgt taagacggct ccgggaaaaa agaggccggt | 2640 |
| agagcactct cctgtggagc cagactcctc ctcgggaacc ggaaaggcgg gccagcagcc | 2700 |

-continued

```
tgcaagaaaa agattgaatt ttggtcagac tggagacgca gactcagtac ctgaccccca    2760
gcctctcgga cagccaccag cagcccctc tggtctggga actaatacga tggctacagg     2820
cagtggcgca ccaatggcag acaataacga gggcgccgac ggagtgggta attcctccgg    2880
aaattggcat tgcgattcca catggatggg cgacagagtc atcaccacca gcacccgaac    2940
ctgggccctg cccacctaca caaccacct ctacaaacaa atttccagcc aatcaggagc     3000
ctcgaacgac aatcactact ttggctacag cacccttgg gggtattttg acttcaacag     3060
attccactgc cacttttcac cacgtgactg gcaaagactc atcaacaaca actggggatt    3120
ccgacccaag agactcaact tcaagctctt taacattcaa gtcaaagagg tcacgcagaa    3180
tgacggtacg acgacgattg ccaataacct taccagcacg gttcaggtgt ttactgactc    3240
ggagtaccag ctcccgtacg tcctcggctc ggcgcatcaa ggatgcctcc cgccgttccc    3300
agcagacgtc ttcatggtgc cacagtatgg atacctcacc ctgaacaacg ggagtcaggc    3360
agtaggacgc tcttcattt actgcctgga gtactttcct tctcagatgc tgcgtaccgg    3420
aaacaacttt accttcagct cacttttga ggacgttcct ttccacagca gctacgctca     3480
cagccagagt ctggaccgtc tcatgaatcc tctcatcgac cagtacctgt attacttgag    3540
cagaacaaac actccaagtg aaccaccac gcagtcaagg cttcagtttt ctcaggccgg     3600
agcgagtgac attcgggacc agtctaggaa ctggcttcct ggaccctgtt accgccagca    3660
gcgagtatca aagacatctg cggataacaa caacagtgaa tactcgtgga ctggagctac    3720
caagtaccac ctcaatggca gagactctct ggtgaatccg ccatggcaa ccacaaggaa     3780
cgatgaagaa aagttttttc ctcagagcgg ggttctcatc tttgggaagc aaggctcaga    3840
gaaaacaaat gtgaacattg aaaaggtcat gattacagac gaagaggaaa tcggaacaac    3900
caatcccgtg gctacggagc agtatggttc tgtatctacc aacctccaga gaggcaacag    3960
acaagcagct accgcagatg tcaacacaca aggcgttctt ccaggcatgg tctggcagga    4020
cagagatgtg taccttcagg ggcccatctg ggcaaagatt ccacacacgg acggacattt    4080
tcacccctct cccctcatgg gtggattcgg acttaaacac cctcctccac agattctcat    4140
caagaacacc ccgtacctg cgaatccttc gaccaccttc agtgcggcaa agtttgcttc     4200
cttcatcaca cagtactcca cgggacacgg tcagcgtgga gatcgagtgg gagctgcaga    4260
aggaaaacag caaacgctgg aatcccgaaa ttcagtacac ttccaactac aacaagtctg    4320
ttaatcgtgg acttaccgtg gatactaatg gcgtgtattc agagcctcgc cccattggca    4380
ccagataccct gactcgtaat ctgtaattgc ttgttaatca ataaaccgtt taattcgttt   4440
cagttgaact ttggtctctg cgtatttctt tcttatctag tttccatggc tacgtagata    4500
agtagcatgg cgggttaatc attaactaca aggaacccct agtgatggag ttggccactc    4560
cctctctgcg cgctcgctcg ctcactgagg ccgggcgacc aaaggtcgcc cgacgcccgg    4620
gctttgcccg ggcggcctca gtgagcgagc gagcgcgcag agagggagtg gccaa         4675
```

<210> SEQ ID NO 2
<211> LENGTH: 26
<212> TYPE: DNA
<213> ORGANISM: Artificial
<220> FEATURE:
<223> OTHER INFORMATION: PCR primer designated as REPF to amplify Rep78 gene -continued

```
<400> SEQUENCE: 2
gggaggtttg agatctcagc cgccat                                          26

<210> SEQ ID NO 3
<211> LENGTH: 26
<212> TYPE: DNA
<213> ORGANISM: Artificial
<220> FEATURE:
<223> OTHER INFORMATION: PCR primer designated as REPR to amplify Rep78
      gene

<400> SEQUENCE: 3
ataaccatcg gcatgcatac ctgatt                                          26

<210> SEQ ID NO 4
<211> LENGTH: 9
<212> TYPE: DNA
<213> ORGANISM: Artificial
<220> FEATURE:
<223> OTHER INFORMATION: EcoRV linker

<400> SEQUENCE: 4 gtcgatatc                                                              9

<210> SEQ ID NO 5
<211> LENGTH: 9
<212> TYPE: DNA
<213> ORGANISM: Artificial
<220> FEATURE:
<223> OTHER INFORMATION: EcoRN linker

<400> SEQUENCE: 5 gacgatatc                                                              9

<210> SEQ ID NO 6
<211> LENGTH: 10
<212> TYPE: DNA
<213> ORGANISM: Artificial
<220> FEATURE:
<223> OTHER INFORMATION: EcoRV linker

<400> SEQUENCE: 6
catggatatc                                                            10

<210> SEQ ID NO 7
<211> LENGTH: 21
<212> TYPE: DNA
<213> ORGANISM: Artificial
<220> FEATURE:
<223> OTHER INFORMATION: PCR primer designated as 82 which anneals with
      intergration unit

<400> SEQUENCE: 7
aggaacccct agtgatggag t                                               21

<210> SEQ ID NO 8
<211> LENGTH: 21
<212> TYPE: DNA
<213> ORGANISM: Artificial
<220> FEATURE:
<223> OTHER INFORMATION: PCR primer designated as 1722 which anneals
      with AAVS1 region
```

-continued

```
<400> SEQUENCE: 8
ccatcctaag aaacgagaga t                                              21

<210> SEQ ID NO 9
<211> LENGTH: 21
<212> TYPE: DNA
<213> ORGANISM: Artificial
<220> FEATURE:
<223> OTHER INFORMATION: PCR primer designated as 79 to amplify AAVS1
      region used as a probe

<400> SEQUENCE: 9
actttgagct ctactggctt c                                              21

<210> SEQ ID NO 10
<211> LENGTH: 18
<212> TYPE: DNA
<213> ORGANISM: Artificial
<220> FEATURE:
<223> OTHER INFORMATION: PCR primer designated as 80 to amplify AAVS1
      region used as a probe

<400> SEQUENCE: 10
ggaggatccg ctcagagg                                                  18

<210> SEQ ID NO 11
<211> LENGTH: 22
<212> TYPE: DNA
<213> ORGANISM: Artificial
<220> FEATURE:
<223> OTHER INFORMATION: Designed oligonucleotide to introduce mutation
      into Rep78 gene

<400> SEQUENCE: 11
gccaggtacg gagagctggt cg                                             22
```